(12) United States Patent
Tseng et al.

(10) Patent No.: US 9,259,193 B2
(45) Date of Patent: Feb. 16, 2016

(54) PROJECTION METHOD OF 3D RAY TRACING

(71) Applicant: INSTITUTE OF NUCLEAR ENERGY RESEARCH ATOMIC ENERGY COUNCIL, EXECUTIVE YUAN, Taoyuan County (TW)

(72) Inventors: Fan-Pin Tseng, Taipei (TW); Tien-Hsiu Tsai, Taoyuan County (TW); Meei-Ling Jan, Taoyuan County (TW)

(73) Assignee: INSTITUTE OF NUCLEAR ENERGY RESEARCH ATOMIC ENERGY COUNCIL, EXECUTIVE YUAN, Taoyuan County (TW)

( * ) Notice: Subject to any disclaimer, the term of this patent is extended or adjusted under 35 U.S.C. 154(b) by 254 days.

(21) Appl. No.: 14/027,631

(22) Filed: Sep. 16, 2013

(65) Prior Publication Data

US 2014/0138554 A1 May 22, 2014

(30) Foreign Application Priority Data

Nov. 20, 2012 (TW) .............................. 101143281 A

(51) Int. Cl.
*G06K 9/00* (2006.01)
*A61B 6/03* (2006.01)
*G06T 15/06* (2011.01)
*A61B 6/00* (2006.01)
*H05G 1/70* (2006.01)

(52) U.S. Cl.
CPC ................. *A61B 6/037* (2013.01); *A61B 6/032* (2013.01); *G06T 15/06* (2013.01)

(58) Field of Classification Search
CPC .............. A61B 6/00; A61N 5/00; G06T 15/00
USPC ............ 382/128–134; 378/63, 92, 98.4, 98.9, 378/101, 901; 600/310, 407, 436, 473
See application file for complete search history.

(56) References Cited

U.S. PATENT DOCUMENTS 6,196,715 B1 * 3/2001 Nambu .................... A61B 6/00
378/11

\* cited by examiner

*Primary Examiner* — Abolfazl Tabatabai
(74) *Attorney, Agent, or Firm* — WPAT, PC; Justin King

(57) ABSTRACT

The present invention provides a projection method of 3D ray tracing, so as to construct a geometric factor required for the reconstruction of a medical image in the imaging field. The present invention mainly projects a radiation field and a voxel detected by each detector on two 2D planes, then calculates the geometric ratio of a rectangular unit, corresponding to each voxel on the two 2D planes, to the radiation field, respectively, and multiplies the geometric ratios to obtain a sub-geometric factor with respect to the voxel. The sub-geometric factors $g_{ij}$ of all voxels i corresponding to all detectors j are combined to form a geometric factor matrix $G_{ij}$.

25 Claims, 16 Drawing Sheets

PROJECTION METHOD OF 3D RAY TRACING

BACKGROUND OF THE INVENTION

1. Field of Invention

The present invention relates to an image reconstruction technology, and more particularly to a projection method of 3D ray tracing applicable to image reconstruction.

2. Related Art

With the development of science and technology, a medical image becomes an effective diagnosis tool developed in modern times. The principle of a medical image involves establishing a mathematical model by using signals received by detectors during imaging and then reconstructing a 3D image by using an image reconstruction technology. To achieve a desirable image quality, technical improvements in hardware, the technology of establishing a reconstructed mathematical model, and the technology for finding a numerical solution, are all very important links. When a matrix model for describing the physical phenomenon of a system is more precise, the reconstructed image is more correct. A system matrix is subject to many factors such as penetration, detection efficiency, and spatial geometry. Therefore, the computation of a system matrix takes most of the time spent for the reconstruction. The focuses in the early development of the reconstruction technology are how to achieve effective storage and reduce computation. It becomes a trend in the development of the technology to introduce a precise model to the reconstruction technology. By comparison, conventional geometric modeling achieves low resolutions and will gradually fall short to meet the demands of practical applications in the future.

The description of image reconstruction can be represented by the following equation:

$$[P]_{m \times n}[\bar{f}_i]_{n \times 1} = [\bar{C}_j]_{m \times 1},$$

where m denotes the total number of rays, that is, the number of ray responses that the system is capable to generate, for example, a LOR (line of response) in a positron emission tomography (PET) system, n denotes the total number of voxels, P denotes the model of the detection system, $\bar{f}_i$ denotes an image to be reconstructed, and $\bar{C}_j$ denotes a detection result detected by a detection module.

The main component of $P^{m \times n}$ is a geometric distribution phenomenon, in which the basic definition of the matrix G of the spatial distribution is as follows:

$$G_{m \times n} = \begin{pmatrix} & & \\ & g_{ij} & \\ & & \end{pmatrix}_{m \times n},$$

where $g_{ij}$ represents a sensed geometric detection effect of the ith voxel with respect to the jth ray. Because a detector, at a different position, has a different probability to receive various rays, the information of $g_{ij}$ needs to be fed back to the reconstruction process to correct the differences of spatial distribution, and is also referred to as a geometric factor.

Ray tracing is a conventional technology, and the specific optimized implementation of the process can be referred to the reference by Siddon R. L. (1985), which has gained wide use already. The ray tracing technology has significant influences and serves as the basis for the development of all types of image reconstruction technologies in the early period. Nowadays this technology is still used in physical calibration of crystal penetration or simulation of the trajectory a photon in space.

In ray tracing, according to the path of a detection ray in space, the length of the line segment passing through the voxel is taken as the geometric factor, or the length of a ray passing through the entire image space (field of view, FOV) is divided by the length of the ray passing through the image unit as an approximate value of the geometric factor. In this approach, a discrete-continuous problem occurs, when lines connecting the centers of detectors are used for approximation, the phenomenon that detectors cover an area fail to be described, and at the same time non-uniform model of source is fail to be described. When a voxel size is smaller than a detector, some voxels are evenly not passed through. To solve these problems, the number of detection rays needs to be increased, that is, to become sub-samples of detector. For example, the approach of Huesman R. H. (2000) is applicable to nuclear medicine imaging, in which a system model is introduced. Although a more accurate image result can be calculated, the computation cost grows geometrically. By taking this reference document as an example, when each detection unit is divided into 3×3 sub-detectors, because two group of detection units are divided by 9 times, and photons are received in pair, the total number of detection rays becomes 729 sub-rays as large. Although compression and simplification can be done by using the slope and ratio of detection rays, the effect is limited with respect to the price of $O(n^4)$. A ray tracing model is simple and has the advantages in computation, but to meet higher and higher requirements for the accuracy of imaging result, the technology needs to perform reconstruction processing on multiple detection sub-rays, the computation time is significantly increased, making it inapplicable in practice.

According to the accuracy demands in reconstruction, detection rays are divided into multiple detection sub-rays for computation, the computation cost becomes very high and makes it very difficult to apply the new-generation model-based image reconstruction technology in industry. Therefore, as for most commercially available imaging systems at present, to obtain an image result rapidly, a compromise is made with an image with a barely acceptable resolution, and a shift and add algorithm or conventional ray tracing is still used as the kernel for reconstruction.

SUMMARY OF THE INVENTION

The present invention provides a geometric distribution method for a computational imaging system for use in image reconstruction, which is applicable to the reconstruction problems for X-ray imaging, positron imaging or nuclear medicine imaging. Compared with an existing ray tracing algorithm, the present invention is capable of calculating geometric factors of nearly an infinite number of detection sub-rays within an acceptable computation time, significantly improving the accuracy, and introducing other physical information such as emission source distribution information in a geometric spatial distribution model, so as to serve as the basic kernel for a new-generation model-based image reconstruction technology.

In an embodiment, the present invention provides a projection method of 3D ray tracing, which includes the following steps: providing an emission source to generate a radiation field to be projected to a detection module, the detection module having a plurality of detectors j arranged in an array; defining a 3D space formed by a first axis, a second axis, and a third axis between the emission source and the plurality of detectors arranged in an array, the 3D space having a plurality of voxels i stacked to form a three-dimensional space array, the emission source being set in the direction of the third axis, and a sensing plane of the plurality of detectors corresponding to a first plane defined by the first axis and the second axis, so as to sense the radiation field; defining that a sub-radiation field exists between each detector that senses the radiation field and the emission source; providing a computational processing unit for deduction, so as to obtain a sub-geometric factor $g_{ij}$ corresponding to each voxel i of each detector j in a corresponding sub-radiation field, the deduction further including the following steps: projecting the sub-radiation field corresponding to each detector and the plurality of voxels on a second plane formed by the first axis and the third axis and on a third plane formed by the second axis and the third axis, respectively, so that the computational processing unit of each detector has a corresponding plane radiation field and an adjacent plurality rows of one-dimensional rectangular array arranged into a 2D plane on the second plane and the third plane, respectively, each row of one-dimensional rectangular array has a plurality of rectangular units arranged adjacent to each other, and each voxel corresponds to one rectangular unit on the second plane and corresponds to one rectangular unit on the third plane; computing a geometric ratio of each rectangular unit inside an area covered by each row of one-dimensional rectangular array of the plane radiation field corresponding to each detector on the second plane and the third plane, respectively; and multiplying the geometric ratios of the rectangular units corresponding to each other on the second plane and the third plane to obtain the sub-geometric factor $g_{ij}$ of the voxel corresponding to each detector; and combining the sub-geometric factors $g_{ij}$ of all detectors j with respect to all voxels i to form a geometric factor matrix $G_{ij}$.

In another embodiment, the present invention further provides a projection method of 3D ray tracing, which includes the following steps: providing an emission source disposed (like positron-electron annihilation) between a first detection module and a second detection module, so as to generate a radiation field to be projected to the first detection module and the second detection module, and the first detection module and the second detection module having a plurality of detectors j arranged in an array, respectively, so as to form j×j detector pairs; defining a 3D space formed by a first axis, a second axis, and a third axis between the emission source and the plurality of detectors arranged in an array, the 3D space having a plurality of voxels i stacked to form a three-dimensional space array, a sensing plane of the plurality of detectors corresponding to a first plane defined by the first axis and the second axis, so as to sense the radiation field, each sensed radiation field being obtained by one detector on the first detection module and another detector on the second detection module at the same time; defining that corners corresponding to each pair of detectors that sense the radiation field are connected to form a sub-radiation field; providing a computational processing unit for deduction, so as to obtain a sub-geometric factor $g_{ij}$ corresponding to each voxel i of each detector pair in a corresponding sub-radiation field, the deduction further including the following steps: projecting the sub-radiation field corresponding to each detector pair and the plurality of voxels on a second plane formed by the first axis and the third axis and on a third plane formed by the second axis and the third axis, respectively, so that the computational processing unit of each detector pair has a corresponding plane radiation field and an adjacent plurality rows of one-dimensional rectangular array arranged into a 2D plane on the second plane and the third plane, respectively, each row of one-dimensional rectangular array has a plurality of rectangular units arranged adjacent to each other, and each voxel corresponds to one rectangular unit on the second plane and corresponds to one rectangular unit on the third plane; computing a geometric ratio of each rectangular unit inside an area covered by each row of one-dimensional rectangular array of the plane radiation field corresponding to each detector pair on the second plane and the third plane, respectively; and multiplying the geometric ratios of the rectangular units corresponding to each other on the second plane and the third plane to obtain the sub-geometric factor $g_{ij}$ of the voxel corresponding to each detector pair; and combining the sub-geometric factors $g_{ij}$ of all detector pairs with respect to all voxels i to form a geometric factor matrix $G_{ij}$.

BRIEF DESCRIPTION OF THE DRAWINGS

The present invention will become more fully understood from the detailed description given herein below for illustration only, and thus are not limitative of the present invention, and wherein.

DETAILED DESCRIPTION OF THE INVENTION

Figure 1:
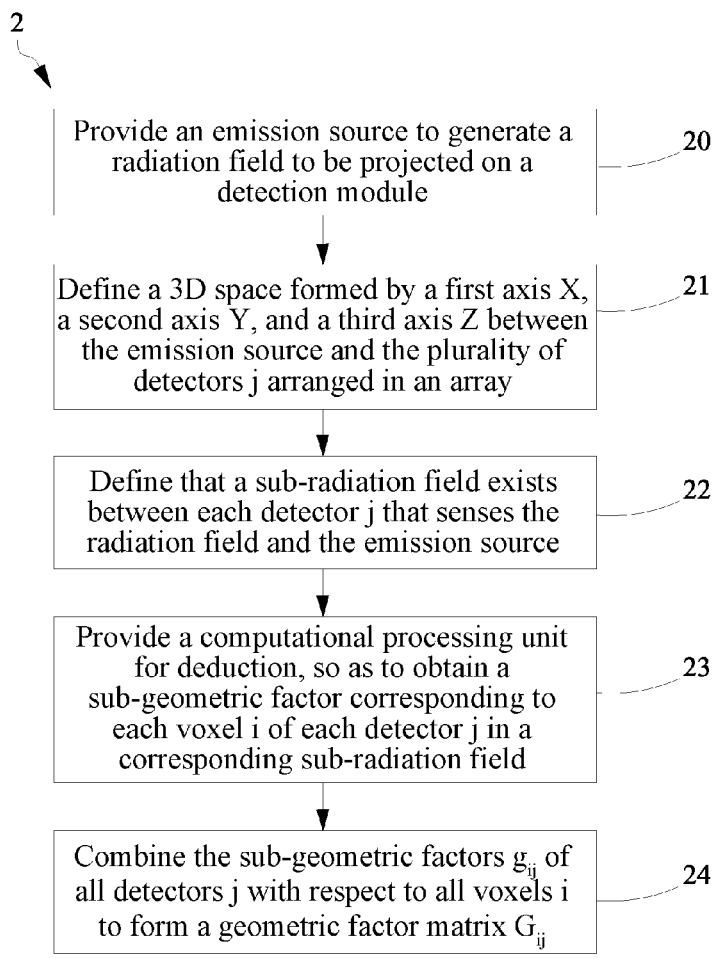
FIG. 1 is a schematic flow chart of a projection method of 3D ray tracing according to the present invention.
Figure 2:
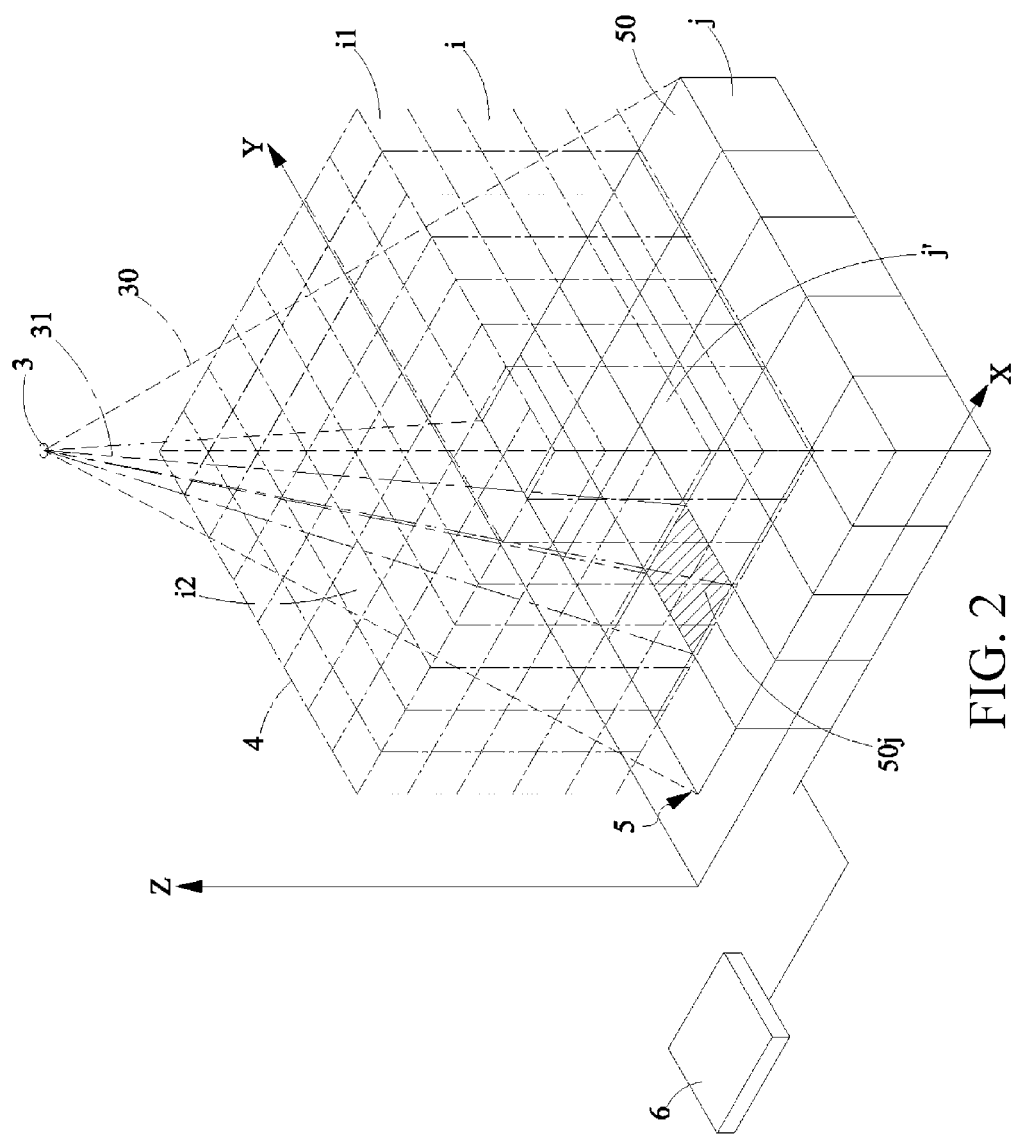
FIG. 2 is a schematic view of the relationship between an emission source and detectors according to the present invention.

Referring to FIG. 1 and FIG. 2, FIG. 1 is a schematic flow chart of a projection method of 3D ray tracing according to the present invention, and FIG. 2 is a schematic view of the relationship between an emission source and detectors according to the present invention. The method for constructing an image reconstruction geometric factor 2 includes the following steps. First, in Step 20, an emission source 3 is provided to generate a radiation field 30 to be projected on a detection module 5. In this embodiment, the emission source 3 is an emission source capable of generating an X ray, and the detection module 5 is used to detect the X ray generated by the emission source 3. The detection module 5 has a plurality of detectors j arranged in an array. The detector j is a detector formed of a scintillation crystal, the structure of which belongs to the prior art and is not elaborated here. In addition, it should be noted that the position where the emission source 3 is placed is not limited specifically. In this embodiment, the emission source is placed at the central position in the sensing plane corresponding to the detection module 5. It should be noted that although the detection module 5 in this embodiment belongs is utilized for detecting an X ray in an X-ray imaging system, in another embodiment, the detection module 5 can be utilized in a computed tomography system, a single-photon emission computed tomography system or a tomosynthesis imaging system.

Next, in Step 21, a 3D space formed by a first axis X, a second axis Y, and a third axis Z is defined between the emission source 3 and the plurality of detectors j arranged in an array, the 3D space has a plurality of voxels i stacked to form a three-dimensional space array 4, the emission source 3 is set in the direction of the third axis and project the radiation field 30 on a first plane defined by the first axis X and the second axis Y, and a sensing plane 50 of the plurality of detectors j corresponds to the first plane defined by the first axis X and the second axis Y, so as to sense the radiation field 30. Next, as shown in Step 22, it is defined that a sub-radiation field 31 exists between each detector j that senses the radiation field 30 and the emission source 3, where the sub-radiation field 31 is a part of the radiation field 30.

Figure 3:
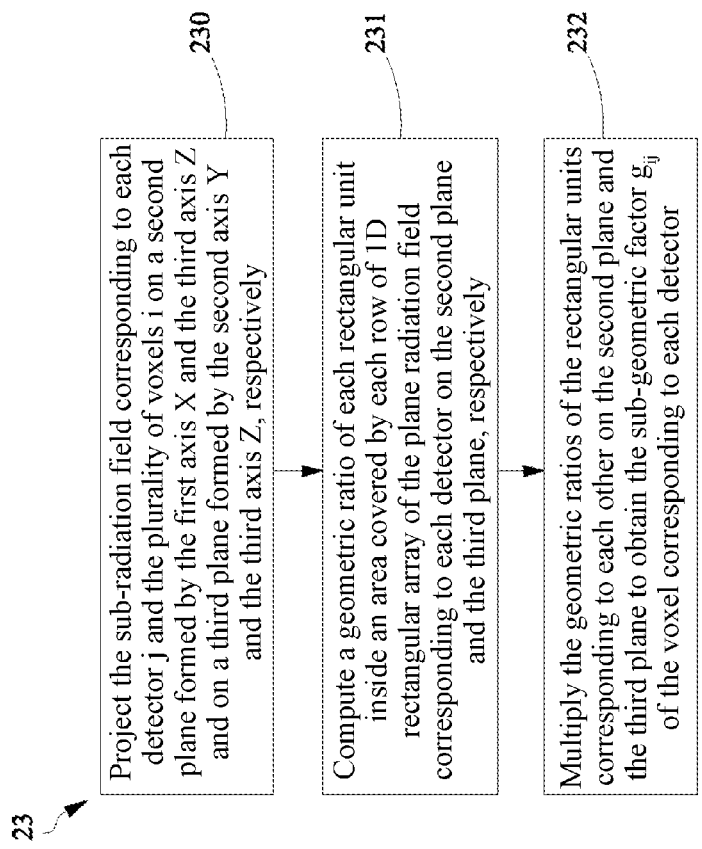
FIG. 3 is a schematic flow chart of the computation of a sub-geometric factor.
Figure 4B:
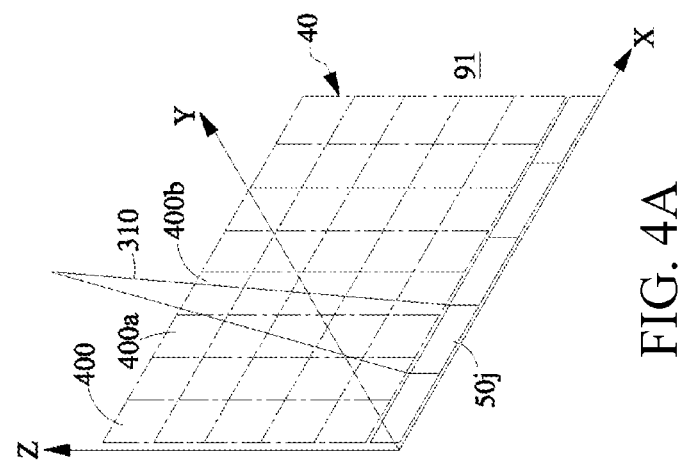
FIG. 4A and FIG. 4B are schematic views of projecting sub-radiation fields and voxels on a second plane and a third plane.
Figure 4A:
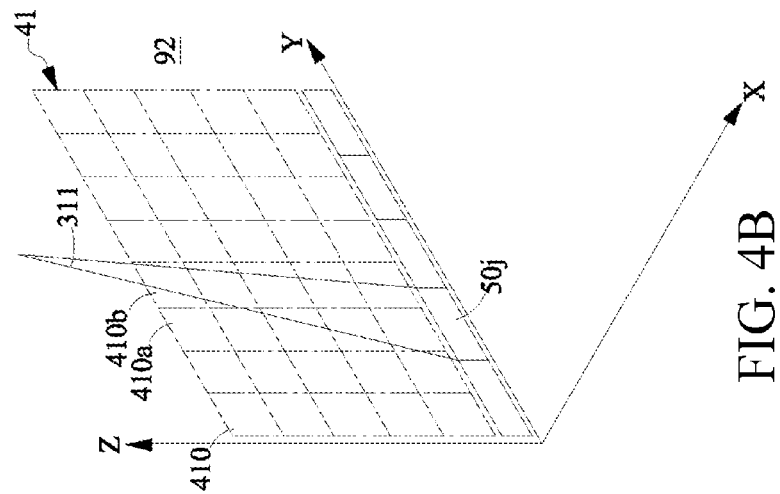

Next, in Step 23, a computational processing unit is provided for deduction, so as to obtain a sub-geometric factor $g_{ij}$ corresponding to each voxel i of each detector j in a corresponding sub-radiation field, and the deduction further includes the following steps. As shown in FIG. 2 and FIG. 3, FIG. 3 is a schematic flow chart of the computation of a sub-geometric factor. First, in Step 230, the sub-radiation field 31 corresponding to each detector j and the plurality of voxels i are projected on a second plane formed by the first axis X and the third axis Z and projected on a third plane formed by the second axis Y and the third axis Z, respectively. As shown in FIG. 4A and FIG. 4B, FIG. 4A and FIG. 4B are schematic views of projecting sub-radiation fields and voxels on the second plane and on the third plane. After the projection, each detector j has a corresponding plane radiation field 310 and arranged into a 2D plane an adjacent plurality rows of one-dimensional rectangular array 40 on the second plane 91, and each row of one-dimensional rectangular array 40 has a plurality of rectangular units 400 arranged adjacent to each other; and similarly, has a corresponding plane radiation field 311 and an adjacent plurality rows of one-dimensional rectangular array 41 arranged into a 2D plane on the second plane 91, and each row of one-dimensional rectangular array 41 has a plurality of rectangular units 410a arranged adjacent to each other. Each voxel i in FIG. 2 corresponds to a rectangular unit 400 on the second plane 91 and corresponds to a rectangular unit 401 on the third plane 92. Referring to FIG. 2, FIG. 4A, and FIG. 4B correspondingly, for example: the i2th voxel corresponds to the rectangular units 400a and 410a.

Referring back to FIG. 3 then, subsequently in Step 231, a geometric ratio of each rectangular unit inside an area covered by each row of one-dimensional rectangular array of the plane radiation field corresponding to each detector is computed on the second plane and the third plane, respectively. In this step, the computational processing unit is capable of executing the technology in Step 231 at the same time, or the computational processing unit is also capable of processing the second plane first and then processing the third plane, which depends on the computational processing capability of the computational processing unit and is not limited.

Figure 5:
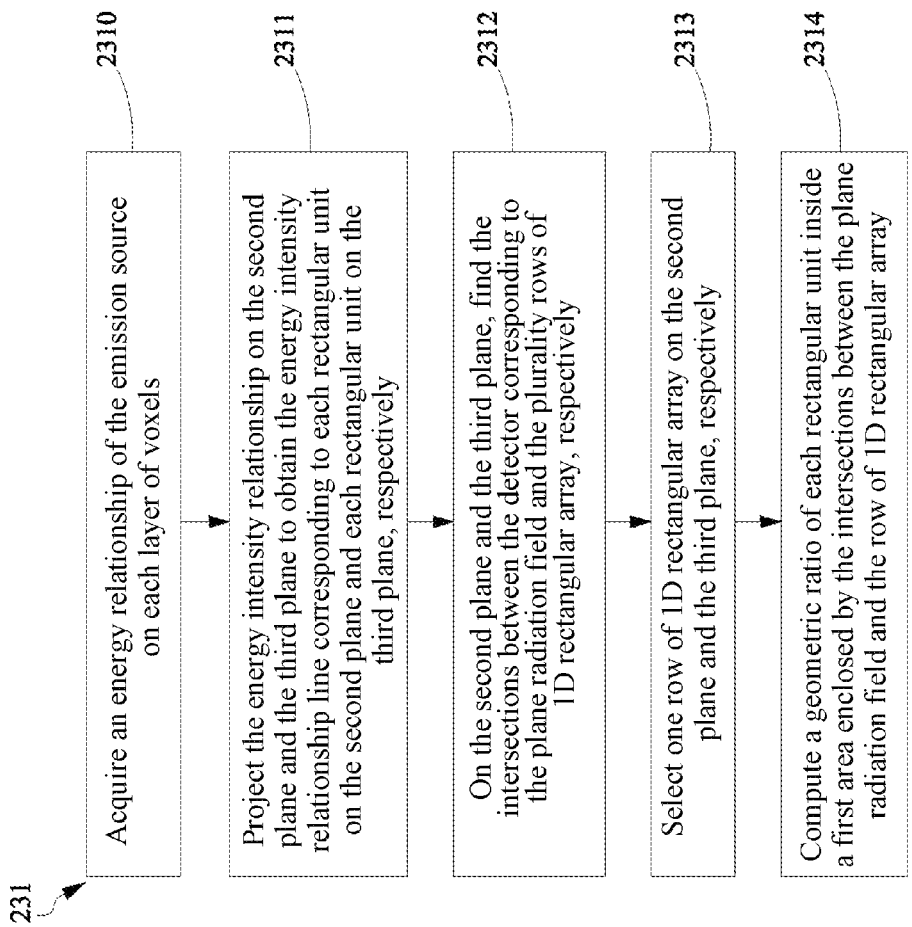
FIG. 5 is a schematic flow chart of the computation of a geometric ratio through computational processing according to the present invention.
Figure 6:
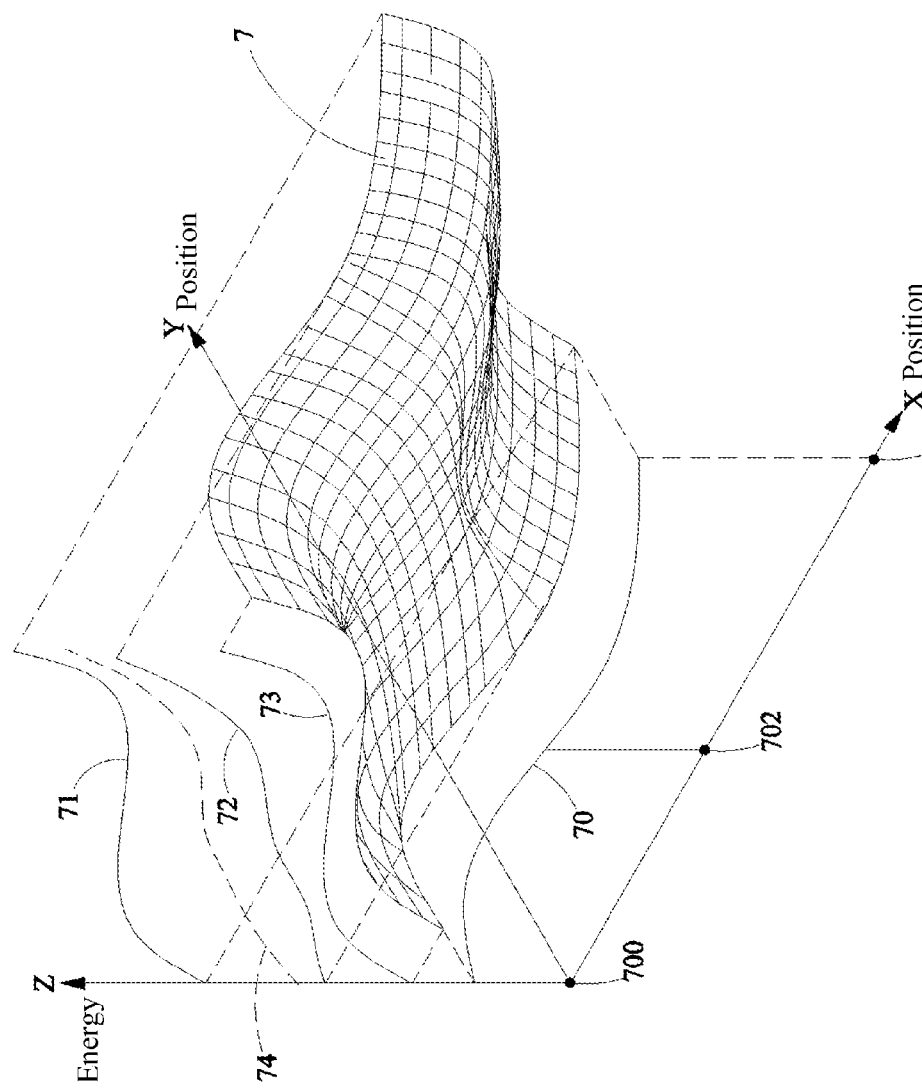
FIG. 6 is an energy intensity relationship diagram of an emission source on one layer of voxels in the Z direction in the three-dimensional space array shown in FIG. 2.

Next, the computational processing of the second plane is used to illustrate Step 231. Referring to FIG. 5, FIG. 5 is a schematic flow chart of the computation of a geometric ratio through computational processing according to the present invention. First, in Step 2310, acquire an energy intensity relationship of the emission source on each layer of voxels. The object of establishing the intensity relationship lies in that the energy intensity of the emission source changes with the distance of projection. As shown in FIG. 6, FIG. 6 is an energy intensity relationship diagram of an emission source on one layer of voxels in the Z direction in the three-dimensional space array 4 shown in FIG. 2. Because of the phenomena that the radiation field emitted by the emission source changes with height and angle and the material of the emission source is uneven, it is not necessarily even at each position on each layer of voxels. Therefore, the energy intensity received at each position (X,Y) in each layer of voxels is not necessarily same. As shown by the curved surface 7 in FIG. 6, it denotes the energy received at the position (X,Y) at the same height along the Z axis of the layer where the i1th voxel belongs in FIG. 2. It should be noted that the energy intensity relationship diagram can be acquired by measuring an emission source in advance or acquired from the specifications of an emission source at delivery.

Next, in Step 2311 in FIG. 5, the energy intensity relationship is projected on the second plane and the third plane to obtain the energy intensity relationship line corresponding to each rectangular unit on the second plane and each rectangular unit on the third plane, respectively. As shown in FIG. 6, to make the energy intensity relationship 7 in FIG. 6 correspond to the relationships of projection on the second plane and the third plane in FIG. 4A and FIG. 4B, the energy intensity relationship 7 in FIG. 6 can be projected on the plane formed by the first axis and the third axis to obtain an energy intensity relationship line 70, and the energy intensity relationship line is used as the energy intensity relationship line corresponding to each row of one-dimensional rectangular array in FIG. 4A; and the energy intensity relationship 7 in FIG. 6 can be projected on a plane formed by the second axis and the third axis to obtain another energy intensity relationship line, which is used as the energy intensity relationship line corresponding to each row of one-dimensional rectangular array in corresponding FIG. 4B. It should be noted that, energy relationship line can be a straight line or a curve. In addition, because the energy intensity relationship between the emission source and each voxel changes with the distance and angle, the two energy intensity relationship lines obtained by projecting the energy intensity relationship 7 in FIG. 6 only correspond to one row of one-dimensional rectangular array in FIG. 4A and FIG. 4B, that is, each row of one-dimensional rectangular array has a corresponding energy intensity relationship line. In addition, in some cases, the projection on a plane does not necessarily obtain a single energy intensity relationship line. For example, on the plane defined by the second axis and the third axis, a plurality of energy intensity relationship lines 71 to 73 is able to be obtained. At this time, through numerical analysis, for example, by taking an average value or through processing in other deduction manners, the energy intensity relationship lines 71 to 73 are associated to a single energy intensity relationship line 74, so that the energy intensity relationship line 74 is used as an energy intensity relationship line corresponding to a specific row of one-dimensional rectangular array in FIG. 4B.

Referring back to FIG. 5 then, next in Step 2312, on the second plane and the third plane, find the intersections between the detector corresponding to the plane radiation field and the plurality rows of one-dimensional rectangular array, respectively. As shown in 7, the projection on the second plane corresponding to FIG. 4A is used for illustration. The plane radiation field 310 and a plurality of rows of one-dimensional rectangular array 40 to 40d have intersections. For example, intersections 410 to 414 exist between the plane radiation field 310 and the rectangular units 400a and 400b on the first row of one-dimensional rectangular array 40; or, for example, intersections 417 to 421 exist between the plane radiation field 310 and rectangular units 400a, 400b, and 400c on the fourth row of one-dimensional rectangular array 40c. After finding the intersection, next, referring back to FIG. 5 then, in Step 2313, one row of one-dimensional rectangular array is selected on the second plane and the third plane, respectively. Next, in Step 2314, a geometric ratio of each rectangular unit inside a first area enclosed by the intersections between the plane radiation field and the row of one-dimensional rectangular array is computed.

Figure 7:
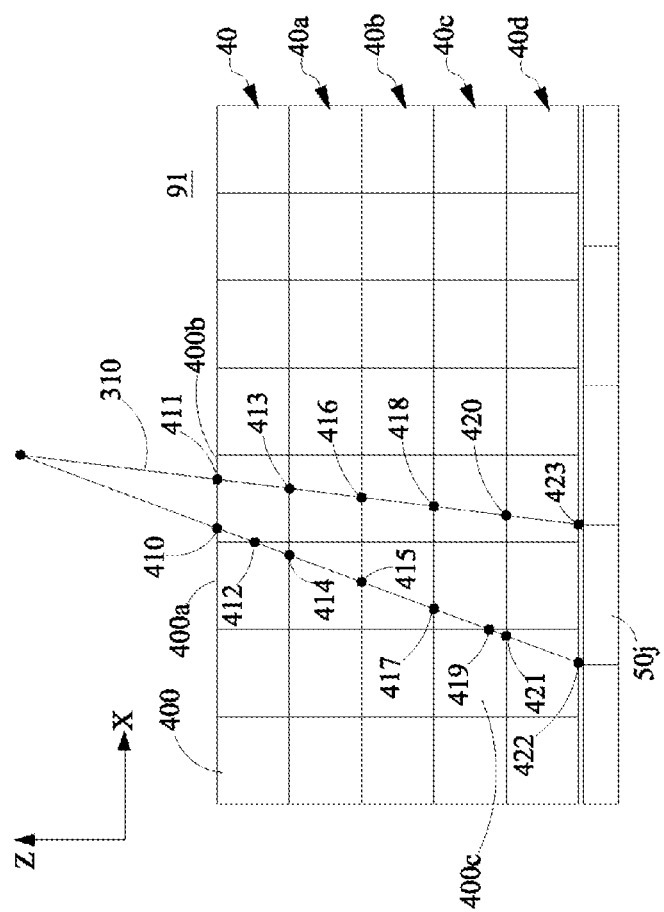
FIG. 7 is a schematic view of projecting sub-radiation fields and voxels on the second plane.
Figure 8A:
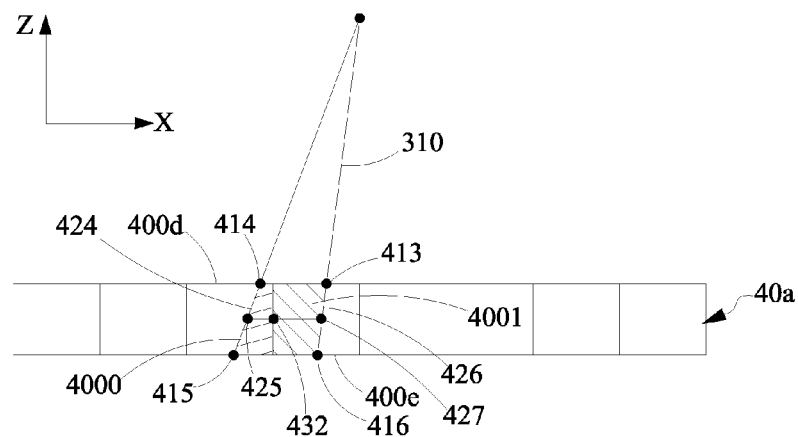
FIG. 8A and FIG. 8B are schematic views of computing the geometric ratio of each rectangular unit for a one-dimensional rectangular array.
Figure 8B:
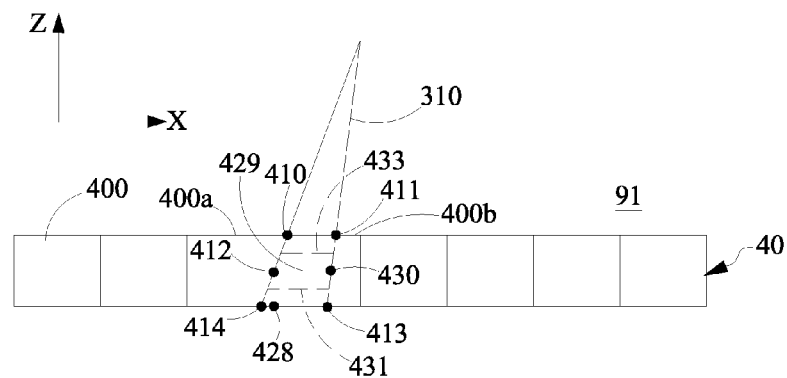

For example, as shown in FIG. 8A, intersections 413 to 416 exist between the rectangular units 400d and 400e in the one-dimensional rectangular array 40a and the plane radiation field 310, and first areas (4000, 4001) are enclosed, in which the area 4000 belongs to the rectangular unit 400d, and the area 4001 belongs to the rectangular unit 400e. It is assumed that the energy intensity relationship line 70 on the XZ plane in FIG. 6 denotes the energy intensity relationship line of one-dimensional rectangular array 40a, and it should be noted that, the energy intensity relationship line denotes the energy distribution at the central position of the one-dimensional rectangular array. Next, in the first area, the midpoint 425 of the side 424 formed by the intersection 414 and the intersection 415 and the midpoint 427 of the side 426 formed by the intersection 413 and the intersection 416 are connected to form a median (425, 427), the starting point 426 and the endpoint 427 of the median (425, 427) correspond to the starting position 700 and the end position 701 of the energy intensity relationship line 70. Therefore, the geometric ratio of the rectangular unit 400d is an integral value of the line segment of the median (425, 427) passing through the area 4000 in FIG. 8A corresponding to the energy intensity relationship line in FIG. 6. For example, in FIG. 8A, the geometric ratio of the rectangular unit 400d is an integral value of the positions 700 to 702 of the line segment (425, 432) corresponding to FIG. 6 to the energy intensity relationship line 70. According to the above manner, it can be similarly computed that the geometric ratio of the rectangular unit 400e is the integral value of the positions 702 to 701 between midpoints 432 and 427 corresponding to FIG. 6 to the energy intensity relationship line 70. As for other rectangular units in the one-dimensional rectangular array 40a, for being not swept by the plane radiation field 310, the corresponding geometric ratio thereof is 0. As shown in FIG. 8B, FIG. 8B is a schematic view of computing the geometric ratio of each rectangular unit in the first row of one-dimensional rectangular array 40. In the embodiment in FIG. 8B, as discussed in FIG. 8A, intersections 410 to 414 exist between the plane radiation field 310 and rectangular units 400a and 400b, but in this embodiment, the plane radiation field 310 and the rectangular units 400a and 400b have an assistant intersection 412 at the side in the Z direction. In this case, the manner for integrating the energy intensity relationship line is slightly different from that in FIG. 8A. The difference is that in this embodiment, a reference line 429 of the assistant intersection 412 is first drawn, which is parallel to the X direction, and the reference line divides the area formed by the intersections 410 to 414 into two blocks: the block (410, 411, 412, and 430) and the block (412, 414, 413, and 430), in which the block (410, 411, 412, and 430) covers the rectangular unit 400b, whereas the block (412, 414, 413, and 430) covers the rectangular units 400a and 400b. Next, an energy intensity relationship line corresponding to the block (410, 411, 412, and 430) and the block (412, 414, 413, and 430) is decided. As the aforementioned energy intensity relationship line corresponds to each row of one-dimensional rectangular array and corresponds to the position of median, the energy intensity relationship line corresponding to the block (410, 411, 412, and 430) and the block (412, 414, 413, and 430) can be decided through interpolation or extrapolation of the energy intensity relationship lines corresponding to the rows of one-dimensional rectangular array 40a or 40b. In the case of the one-dimensional rectangular array 40c in FIG. 7, the reference line formed by the intersection 419 is divided into corresponding energy curves of an upper area and a lower area, which can be obtained through interpolation of the rows of one-dimensional rectangular array 40b and 40d.

Next, the medians 431 and 433 of the block (410, 411, 412, and 430) and the block (412, 414, 413, and 430) are then decided, and at this time, then the geometric ratios of rectangular units 400a and 400b can be found through integration in the manner shown in FIG. 8A. It should be noted that, during the integration on the block (410, 411, 412, and 430) and block (412, 414, 413, and 430) to the corresponding energy intensity relationship lines, the geometric ratios of all blocks of the rectangular unit 400b can be obtained, and therefore the geometric ratio of the entire rectangular unit 400b is the sum of the geometric ratios obtained from the corresponding integration with respect to the rectangular unit 400b of the block (410, 411, 412, and 430) and the block (412, 414, 413, and 430).

In addition, it should be noted that, although the aforementioned energy intensity relationship curved surface corresponds to each layer of voxels, in another embodiment, the curved surface does not correspond to each layer of voxels, and instead, the Z axis between the emission source 3 and the detection module 5 is divided into a plurality of heights, each height corresponds to an energy intensity relationship curved surface, the information of which is stored in the memory, and the number of the plurality of heights depends on the computational capability and the memory space of the computational processing unit 6. In the case of this manner of processing, by taking FIG. 8A and FIG. 8B as an example, after the median (425, 427) and the medians 431 and 433, then the corresponding energy intensity relationship curved surface found according to the position of the median on the Z axis is projected on the plane to obtain an energy intensity relationship line to perform integration computation. Referring back to FIG. 3 then, next, in Step 232, the geometric ratios of the rectangular units corresponding to each other on the second plane and the third plane are multiplied to obtain the sub-geometric factor $g_{ij}$ of the voxel corresponding to each detector. As shown by the examples in FIG. 7, FIG. 8A, and FIG. 8B, the geometric ratio of one detector 50j corresponding to each rectangular unit on the second plane is computed. According to the same manner, the geometric ratio of the rectangular unit covered by the plane radiation field 311 obtained through the projection corresponding to the detector 50*j* on the corresponding third plane shown in FIG. 4B is computed. Next, the rectangular units with the positions corresponding to each other, that is, the geometric ratios of the rectangular units that correspond to the second plane and the third plane of one same voxel are multiplied to obtain the sub-geometric factor $g_{ij}$ of each voxel corresponding to the detector 50*j*. By taking FIG. 2 and corresponding FIG. 4A and FIG. 4B as an example, the geometric ratio of the rectangular unit 400*a* and the geometric ratio of rectangular unit 410*a* are multiplied, that is, the voxel i2 corresponds to the sub-geometric factor $g_{ij}$ of the detector 50*j*.

Referring back to FIG. 2 then, in the end, in Step 24, the sub-geometric factors $g_{ij}$ of all detectors j with respect to all voxels i are combined to form a geometric factor matrix $G_{ij}$.

Figure 9:
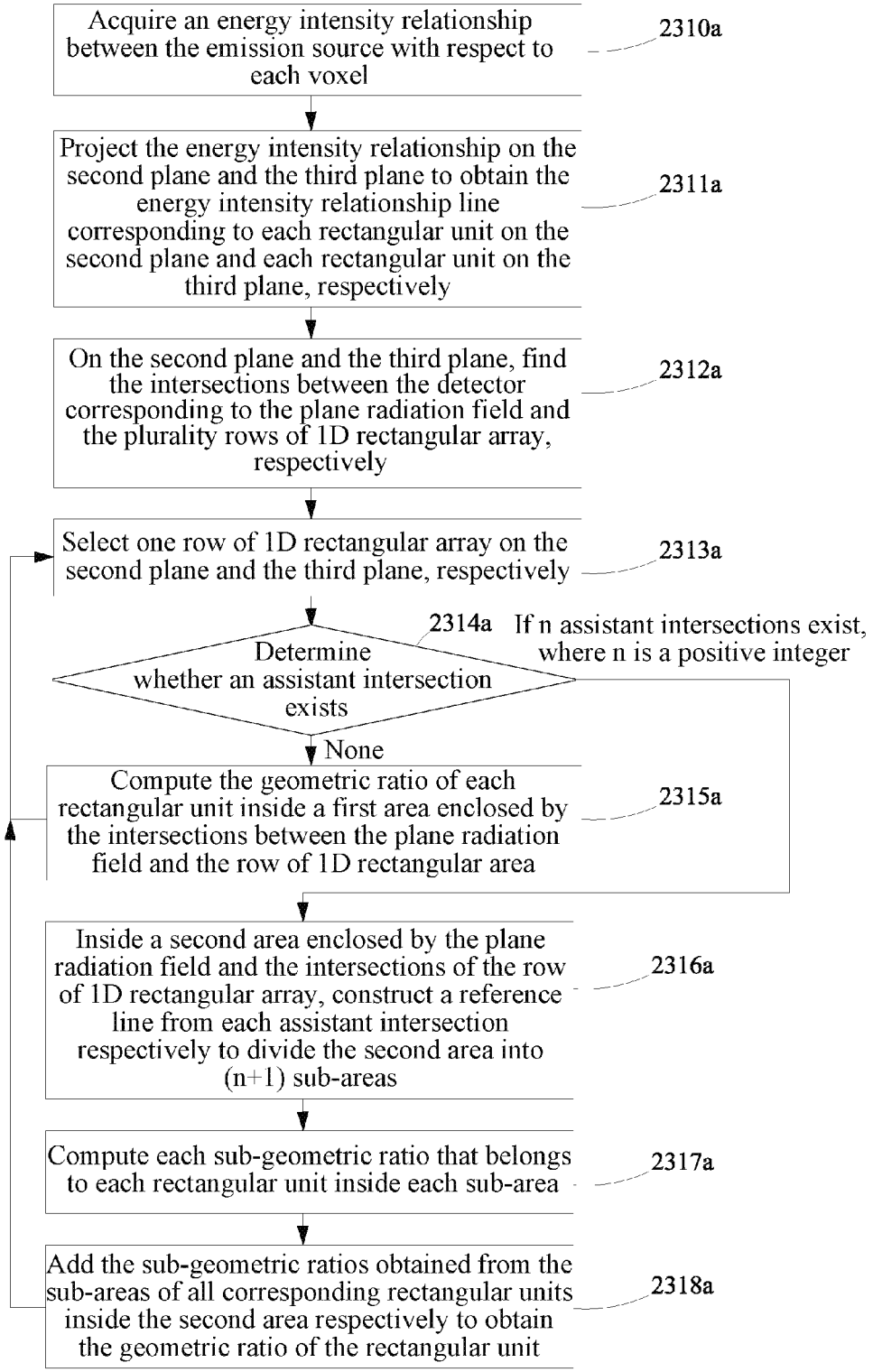
FIG. 9 is a schematic flow chart of the computation of a sub-geometric factor according to another embodiment of present invention.

Referring to FIG. 9, FIG. 9 is a schematic flow chart of the computation of a sub-geometric factor according to another embodiment of the present invention. This embodiment is mainly applicable when the energy intensity relationship lines in FIG. 3A and FIG. 3B are horizontal lines, that is, the radiation fields generated by the emission sources are both even radiation fields for each voxel, and do not change when the position of the voxel becomes different. In this case, Steps 2310*a* to 2313*a* in this process are basically the same as Step 2310 to 2313 in FIG. 5, and the difference lies in that, in this embodiment, after Step 2313*a*, Step 2314*a* is further included, in which it is determined respectively whether assistant intersections exist between the plane radiation field and two sides of the specific rectangular unit inside the one-dimensional rectangular array in the direction of the third axis. The so-called assistant intersection, referring to FIG. 7, is whether an intersection exists between the plane radiation field 310 and the side of each rectangular unit in the direction of the third axis (Z). If an intersection does not exist, in Step 2315*a*, the geometric ratio of each rectangular unit inside a first area enclosed by the intersections between the plane radiation field and the row of one-dimensional rectangular array is computed; and otherwise, if an assistant intersection exists, the process turns to Step 2316*a*.

The detailed computation manner in Steps 2313*a* and 2316*a* is illustrated in the following. As the energy intensity relationship line is a horizontal line, the radiation field of the emission source is even for each voxel, and a sub-ratio factor of each voxel can be computed through the geometric relationship. In corresponding Step 2313*a*, by taking the corresponding rectangular unit of the projection on the second surface as an example, a first row of one-dimensional rectangular array 40 is selected first, and next, in Step 2314*a*, it is determined whether an assistant intersection exists. The so-called assistant intersection is whether an intersection exists between the plane radiation field 310 and the side of each rectangular unit in the direction of the third axis (Z). The first row of one-dimensional rectangular array 40 has one assistant intersection 412. The second row of one-dimensional rectangular array 40*a* does not have an assistant intersection.

Figure 10A:
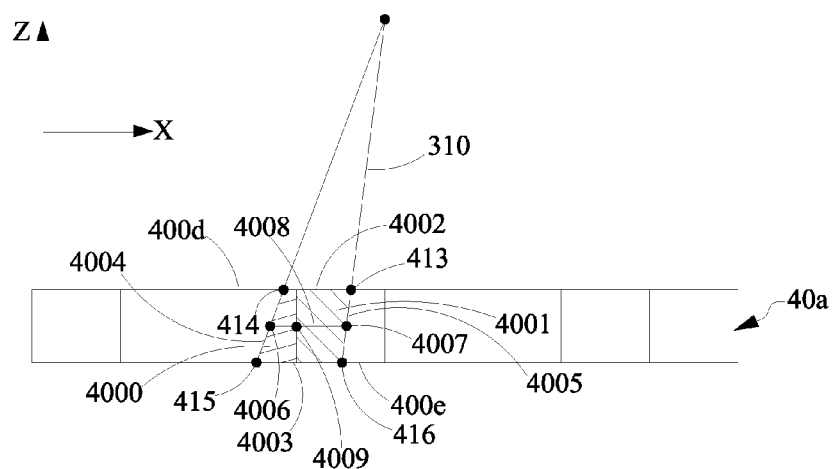
FIG. 10A is a schematic view of the manner of computing the geometric ratio of each rectangular unit when an assistant intersection exists.

The computation manner in Step 2315*a* for the geometric ratio of each rectangular unit when an assistant intersection does not exist is illustrated first. As shown in FIG. 10A, in the second row of one-dimensional rectangular array 40*a*, a first area (4000, 4001) enclosed by the plane radiation field 310 and the intersections 413 to 416 thereof has an upper side 4002 (between intersections 413 and 414), a lower side 4003 (between intersections 415 and 416) and two sides 4004 and 4005. As an assistant intersection does not exist, it is required that the first area (4000, 4001) of each rectangular unit swept by the plane radiation field 310 is a trapezoidal area. The connection between the midpoints 4006 and 4007 of the two sides 4004 and 4005 is defined as the median 4008 of the first area.

As the energy of the emission source is even for each voxel, the geometric ratio of each rectangular unit covered by the plane radiation field 310 can be the ratio between the line length of the median passing through each rectangular unit and the length of the median. By taking FIG. 10A as an example, the geometric ratios of the rectangular units 400*d* and 400*e* covered by the first area (4000, 4001) are ratios of the line length of the median 4008 passing through the rectangular units 400*d* and 400*e* and the length of the median 4008, that is, the ratio of the line length between the midpoint 4006 and the intersection 4009 to the line length of the median 4008 denotes the geometric ratio of the rectangular 400*d*; whereas the ratio of the line length between the intersection 4009 and the midpoint 4007 to the line length of the median 4008 denotes the geometric ratio of the rectangular 400*e*. As for other rectangular units that are not covered by the plane radiation field, the geometric ratio is 0. Step 2315*a* is as illustrated above.

Figure 10B:
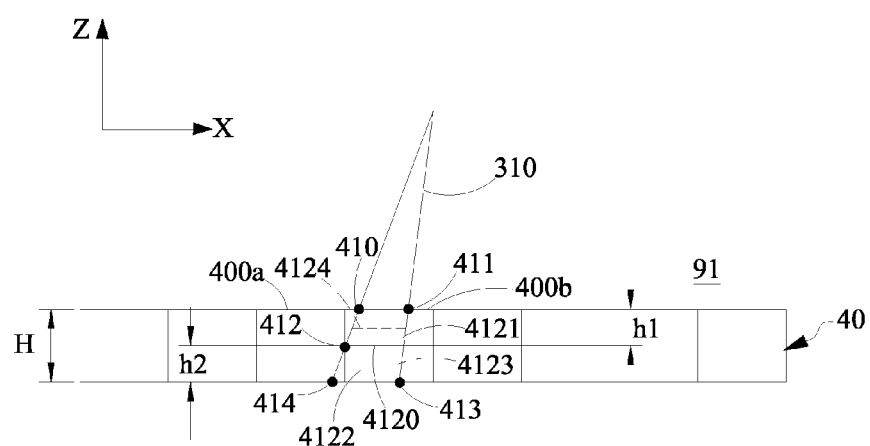
FIG. 10B is a schematic view of the computation of the geometric ratio of a rectangular unit when an assistant intersection exists in FIG. 7 according to a first embodiment.

Next, the method for calculating the geometric ratio of each rectangular unit in the one-dimensional rectangular array of the assistant intersection is illustrated. Referring to FIG. 7 and FIG. 10B, FIG. 10B is a schematic view of the first row of one-dimensional rectangular array 40 in which an assistant intersection exists in FIG. 7. As an assistant intersection 412 exists between the plane radiation field 310 and the one-dimensional rectangular array 40, in Step 2316*a*, if n assistant intersections exist between the plane radiation field and the two sides of the specific rectangular unit inside the one-dimensional rectangular array, inside a second area enclosed by the plane radiation field and the intersections 410 to 414 of the row of one-dimensional rectangular array, a reference line is constructed from each assistant intersection respectively to divide the second area into (n+1) sub-areas, where n is a positive integer. In the embodiment in FIG. 10B, n is 1, but n may also be more than 2. As for the construction of a reference line, as shown in FIG. 10B, a reference line 4120 is generated from the assistant intersection 412 along the first axis (X) to divide the second area into an upper sub-area 4121 and a lower sub-area 4122. The sub-area 4121 is inside the rectangular unit 400*b*, whereas the sub-area 4122 is at the same time inside the rectangular units 400*a* and 400*b*.

Next, in Step 2317*a*, each sub-geometric ratio that belongs to each rectangular unit inside each sub-area is computed respectively. Each sub-area has an upper side, a lower side and two sides, and a median is provided between the midpoints of the two sides. For example, the median of the sub-area 4121 is 4124, whereas the median of the sub-area 4122 is 4123. The sub-geometric ratio of each corresponding rectangular unit inside the sub-area is the product of multiplying the ratio of the line length of the median passing through each rectangular unit to the length of the median and ratio of the height of the sub-area to the height of the rectangular unit. For example, inside the sub-area 4121, as the sub-area 4121 only belongs to the rectangular unit 400*b*, the median length ratio is 1. The sub-geometric ratio affected by the sub-area 4121 of the rectangular unit 400*b* is the product of multiply 1 and the ratio (h1/H) of the height h1 of the sub-area 4121 and the height H of the rectangular unit.

Figure 10C:
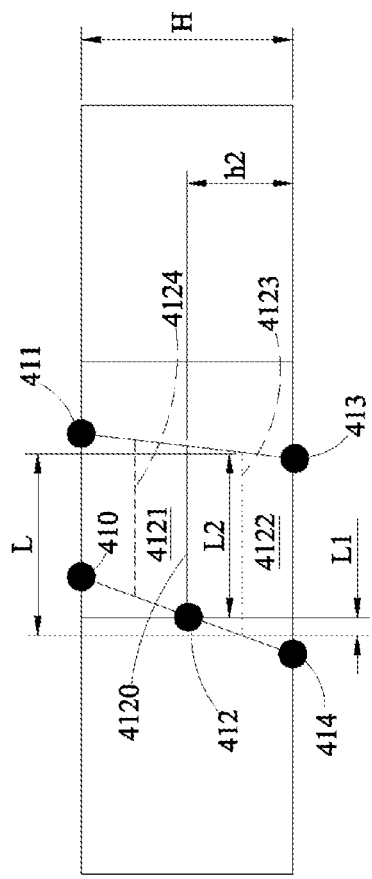
FIG. 10C is a schematic view of the computation of the geometric ratio of a rectangular unit when an assistant intersection exists in FIG. 7 according to a second embodiment.

Similarly, as shown in FIG. 10C, the sub-area 4122 belongs to the rectangular units 400*a* and 400*b*. Therefore, the contribution of the sub-area 4122 to the sub-geometric ratio of the rectangular unit 400*a* is the product of multiplying the ratio (L1/L) of the line length L1 of the median 4123 passing through the rectangular unit 400*a* to the length L of the median 4123 and the ratio (h2/H) of the height h2 of the sub-area 4122 to the height H of the rectangular unit 400a. The contribution of the sub-area 4122 to the sub-geometric ratio of the rectangular unit 400b is the product of multiplying the ratio (L2/L) of the line length L2 of the median 4123 passing through the rectangular unit 400b to the length L of the median 4123 and the ratio (h2/H) of the height h2 of the sub-area 4122 to the height H of the rectangular unit 400a. In the end, in Step 2318a, the sub-geometric ratios obtained from the sub-areas of all corresponding rectangular units inside the second area are added respectively to obtain the geometric ratio of the rectangular unit. In this step, for the rectangular unit 400a, the geometric ratio is equal to the sub-ratio (L1/L)*(h2/H); as the rectangular unit 400b is affected by the sub-areas 4121 and 4122, the geometric ratio thereof is equal to the sub-ratio (L2/L)*(h2/H)+(h1/H). Repeat Step 2313a to Step 2318a till the geometric ratio of each rectangular unit is computed for all the one-dimensional rectangular arrays of the second plane and third plane. Referring back to FIG. 3 then, then in Step 232, the geometric ratios of the rectangular units corresponding to each other on the second plane and the third plane are multiplied to obtain the sub-geometric factor $g_{ij}$ of the voxel corresponding to each detector; next, referring back to FIG. 2 then, in the end, in Step 24, the sub-geometric factors $g_{ij}$ of all detectors j with respect to all voxels i are combined to form a geometric factor matrix $G_{ij}$, the detailed process of which is as discussed above and is not elaborated here.

Figure 11:
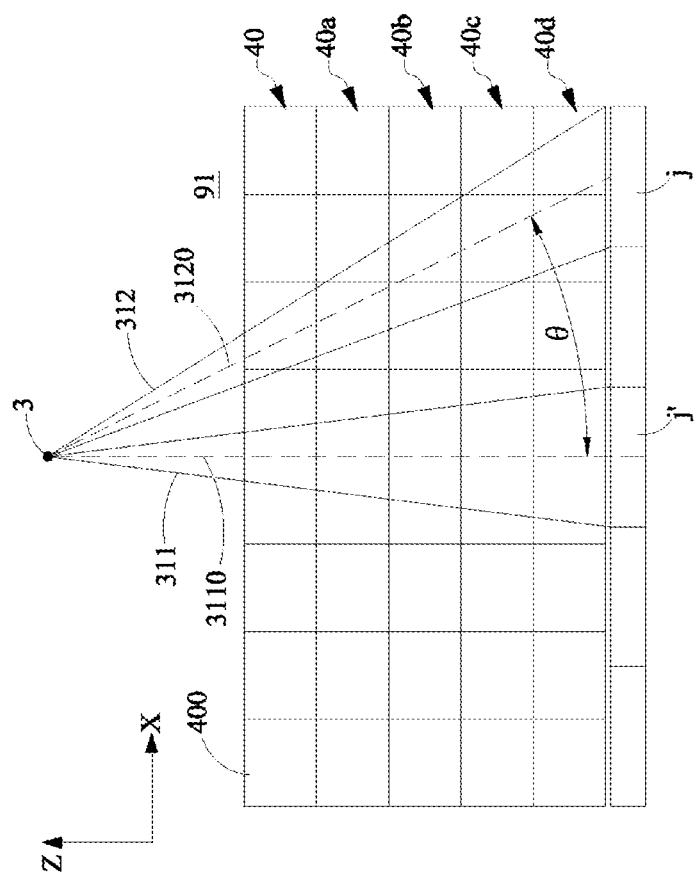
FIG. 11 is a schematic view of the compensation for a sub-geometric factor $g_{ij}$ according to the present invention.

Referring to FIG. 2 and FIG. 11, FIG. 11 is a schematic view of the compensation for the sub-geometric factor $g_{ij}$ according to the present invention. As the relationship between the position of the emission source 3 and the relative position of the detector j is different, the geometric factor needs to compensate for the sub-geometric factor $g_{ij}$ with respect to each voxel obtained for the specific position detector j, so as to increase the accuracy of the geometric factor matrix $G_{ij}$. In an embodiment, the detector j' right below the emission source 3 is used as a reference, during the projection on the plane, an included angle θ between the median 3110 (known) of the plane radiation field 311 corresponding to the detector j' and a median 3120 of a plane radiation field 312 corresponding to other detectors j is computed. At this time, it can be obtained that the length $L_{3120}$ of the median 3120 is the quotient by dividing the length $L_{3110}$ of the median 3110 by cos θ. Next, the sub-geometric factor $g_{ij}$ of each voxel in the corresponding detector j can be divided by ($L_{3110}/L_{3120}$) to obtain the sub-geometric factor $g'_{ij}$ for compensation.

Figure 12A:
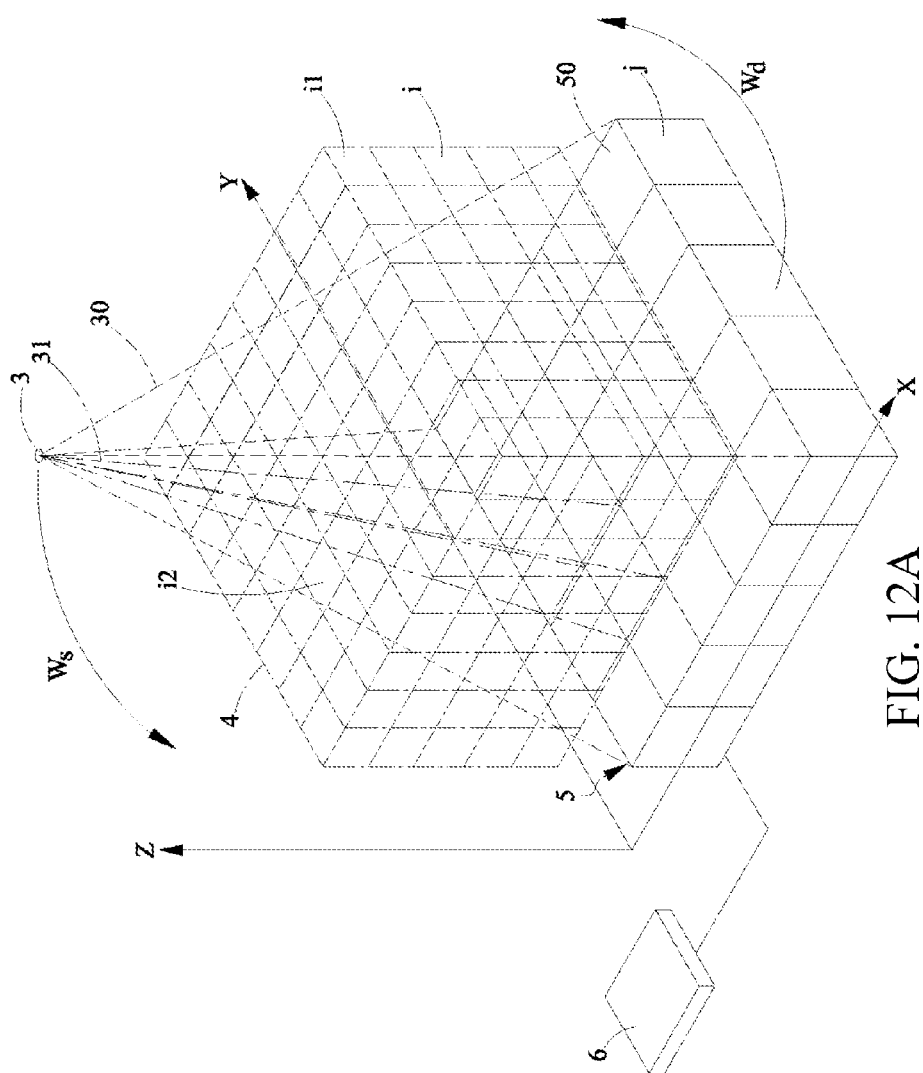
FIG. 12A to FIG. 12D are schematic views when an emission source and detectors revolve according to the present invention.
Figure 12C:
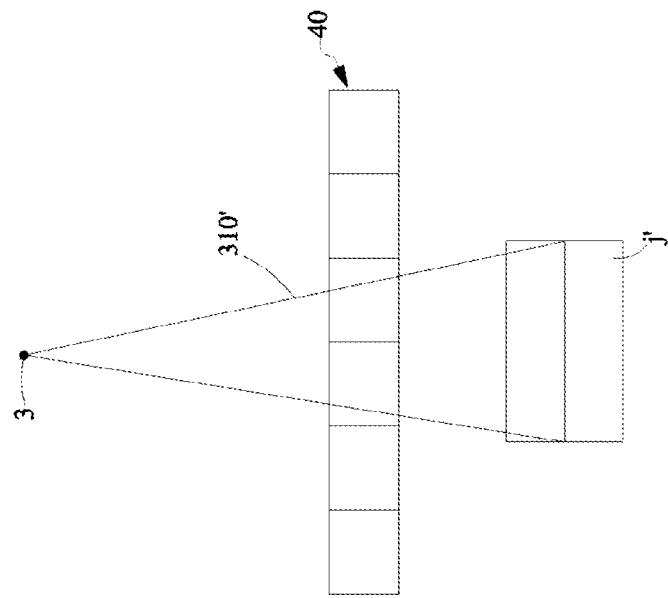
Figure 12B:
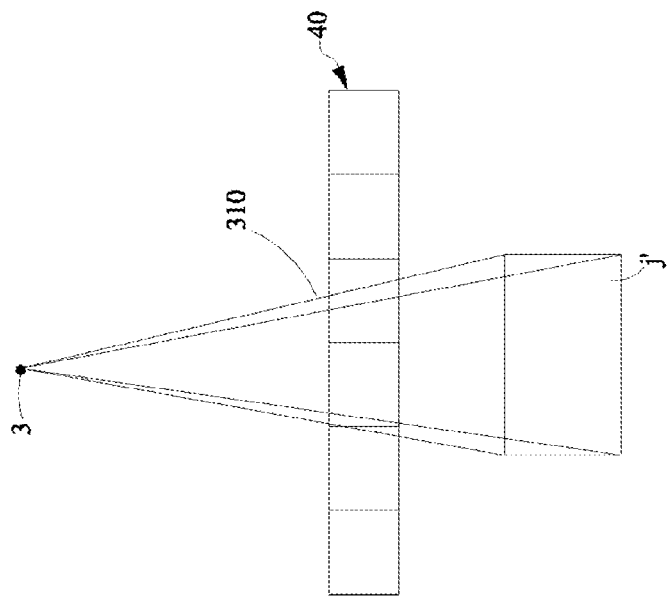
Figure 12D:
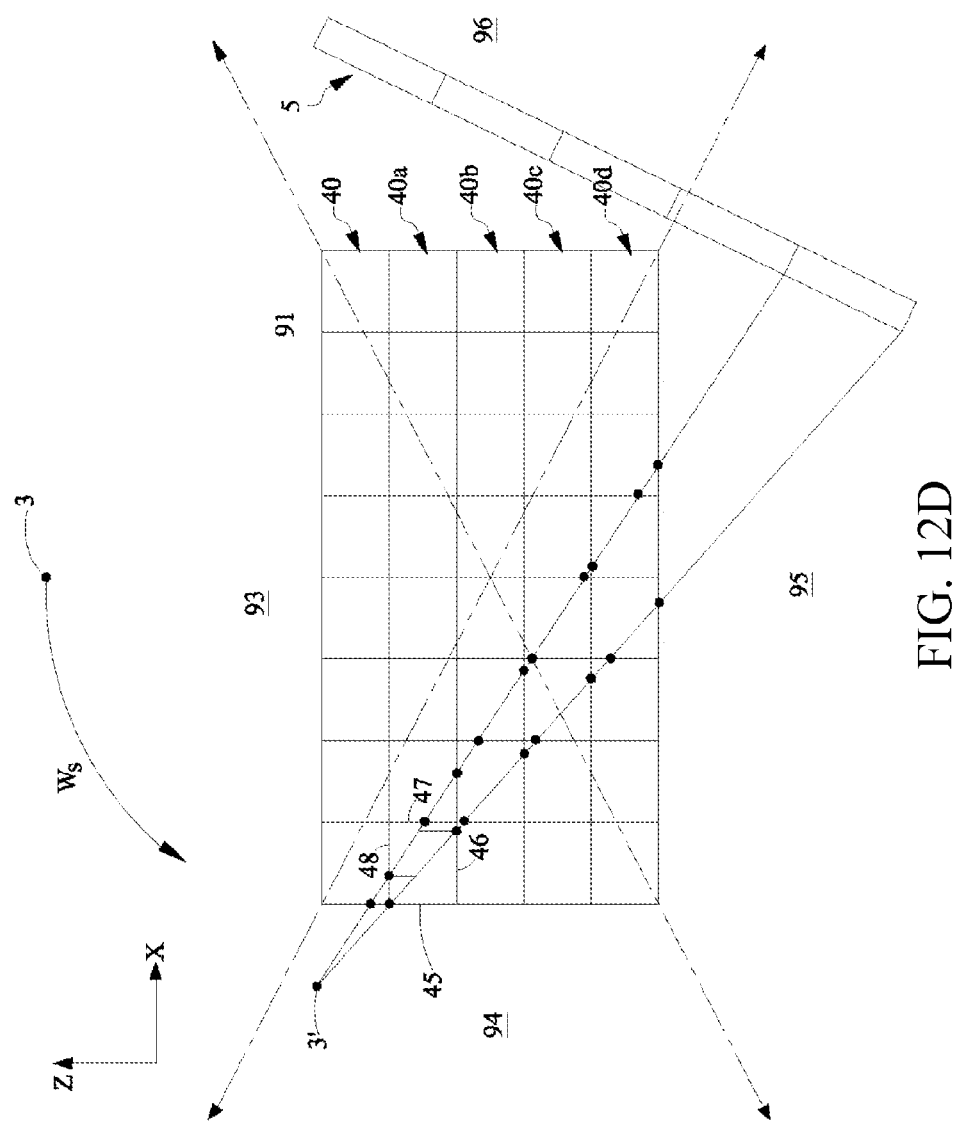

Referring to FIG. 12A to FIG. 12D, FIG. 12A to FIG. 12D are schematic views as an emission source and detectors revolve according to the present invention. In this embodiment, as shown in FIG. 12A, the emission source 3 and the detection module 5 are capable of revolving by 360 degrees. In an embodiment where the emission source 3 revolves, as the voxel i does not revolve, the sub-geometric factor $g_{ij}$ of each voxel corresponding to a different detector at a different revolving angle can be computed by applying the process shown in FIG. 1, FIG. 3, FIG. 5, and FIG. 9. Because the emission source 3 revolves, as shown in FIG. 12A and FIG. 12B, when the emission source 3 revolves to a specific angle, the projected plane radiation field 310 and the detector j' do not only have two lines being connected to two ends of the detector 50j as shown in FIG. 7, and instead, the radiation field in the projected space are connected to four end points of the detector j' after projection, so as to form four lines, which increases the computation complexity. In this embodiment, the case shown in FIG. 12A is simplified, in which, by taking the median of the detector j' as a reference, the plane radiation field 310' of the emission source 3 is connected to the median to form the result as shown in FIG. 12C, thereby simplifying the subsequent process for computing the geometric ratio of each rectangular unit for the one-dimensional rectangular array 40. In addition, to facilitate the computation, as shown in FIG. 12D, with the area where the emission source 3 revolves (which is divided into areas 93 to 96 this embodiment), the definition of the assistant intersection can be changed. In the revolving angle range of the areas 93 and 95, the assistant intersection is defined as the intersection in the direction of sides 45 and 47, while in the revolving angle range of the areas 94 and 96, the assistant intersection is defined as the intersection in the direction of sides 46 and 48. It should be noted that, the object of changing the definition of the assistant intersection in this embodiment is only to facilitate deduction, which is not an essential manner.

Figure 13:
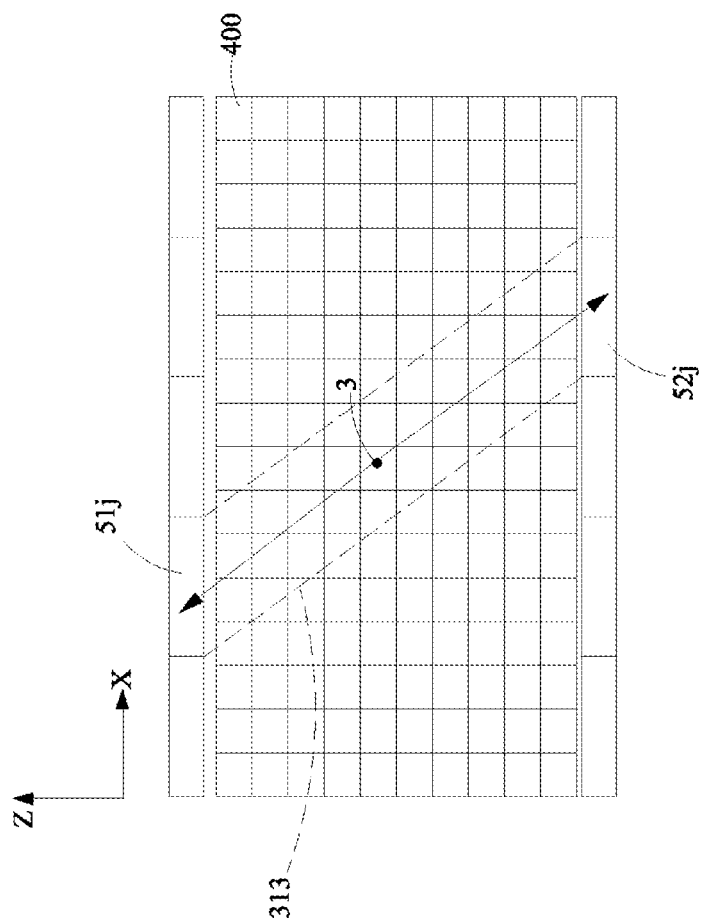
FIG. 13 is another schematic view of the relationship between an emission source and detectors according to the present invention.

Referring to FIG. 13, FIG. 13 is another schematic view of the relationship between an emission source and detectors according to the present invention. In this embodiment, the emission source 3 is disposed between a pair of detection modules 50. The pair of detection modules 50 is detection modules used in positron tomography imaging. (like positron-electron annihilation) A plurality of voxels is defined in the space between the pair of detection modules 50, so as to form a 3D space array. FIG. 13 shows a result of the space array being projected on the plane. In the pair of detection modules 50, j×j detector pairs are provided in total, and within a unit time, each detector pair 51j and 52j senses the radiations emitted by the emission source 3 at the same time to generate a pair of detection responses. After a period of accumulation, a plurality of pairs of detection responses formed as the radiation field generated by the emission source 3 is sensed by the plurality of detector pairs can be recorded. At this time, the sub-geometric factor $g_{ij}$ of each voxel for each detector pair under the emission source can be constructed according to every record, so as to further construct the sub-geometric factors $g_{ij}$ with respect to the voxels i of all detector pairs and combine the sub-geometric factors $g_{ij}$ to form a geometric factor matrix $G_{ij}$.

By taking one record as an example, for a detector pair 51j and 52j, at a specific time, the emission ray emitted by the emission source 3 is sensed to construct the sub-radiation field corresponding to the group detector pair 51j and 52j with respect to the emission source. At this time, the sub-radiation field is defined to be formed by connecting the boundaries of the detector pair 51j and 52j, and when being projected on the plane, so as to obtain the state as shown in FIG. 13. The number 313 denotes a plane radiation field formed when a sub-radiation field is projected on the plane; the number 400 denotes a rectangular unit obtained when the voxel is projected on the plane. For the intersection between the plane radiation field 313 and each one-dimensional rectangular array, the computation manner of obtaining the geometric ratio of each rectangular unit, the sub-geometric factor $g_{ij}$ of each voxel, and the sub-geometric factor $g_{ij}$ of each voxel i to combine them to form a geometric factor matrix $G_{ij}$ is the same as that in the above embodiments, which is not elaborated here.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A projection method of 3D ray tracing, comprising the following steps:

providing an emission source to generate a radiation field to be projected to a detection module, the detection module having a plurality of detectors j arranged in an array;

defining a 3D space formed by a first axis, a second axis, and a third axis between the emission source and the plurality of detectors arranged in an array, the 3D space having a plurality of voxels i stacked to form a three-dimensional space array, the emission source being set in the direction of the third axis, and a sensing plane of the plurality of detectors corresponding to a first plane defined by the first axis and the second axis, so as to sense the radiation field;

defining that a sub-radiation field exists between each detector that senses the radiation field and the emission source;

providing a computational processing unit for deduction, so as to obtain a sub-geometric factor $g_{ij}$ corresponding to each voxel i of each detector j in a corresponding sub-radiation field, the deduction further comprising the following steps:

projecting the sub-radiation field corresponding to each detector and the plurality of voxels on a second plane formed by the first axis and the third axis and on a third plane formed by the second axis and the third axis, respectively, so that each detector has a corresponding plane radiation field and an adjacent plurality rows of one-dimensional rectangular array arranged into a 2D plane on the second plane and the third plane, respectively, each row of one-dimensional rectangular array having a plurality of rectangular units arranged adjacent to each other, and each voxel corresponding to one rectangular unit on the second plane and corresponding to one rectangular unit on the third plane;

computing a geometric ratio of each rectangular unit inside an area covered by each row of one-dimensional rectangular array of the plane radiation field corresponding to each detector on the second plane and the third plane, respectively; and multiplying the geometric ratios of the rectangular units corresponding to each other on the second plane and the third plane to obtain the sub-geometric factor $g_{ij}$ of the voxel corresponding to each detector; and combining the sub-geometric factors $g_{ij}$ of all detectors j with respect to all voxels i to form a geometric factor matrix $G_{ij}$.

2. The projection method of 3D ray tracing according to claim 1, wherein the computing a geometric ratio of each rectangular unit inside an area covered by each row of one-dimensional rectangular array of the plane radiation field further comprises the following steps:

acquiring an energy intensity relationship between the emission source and the detection module at different positions in space; and projecting the energy intensity relationship on the second plane and the third plane to obtain energy intensity relationship lines corresponding to different heights on the second plane and different heights on the third plane, respectively.

3. The projection method of 3D ray tracing according to claim 2, wherein the computing a geometric ratio of each rectangular unit inside an area covered by each row of one-dimensional rectangular array of the plane radiation field further comprises the following steps:

finding intersections between the plane radiation field and the plurality rows of one-dimensional rectangular array on the second plane and the third plane, respectively;

selecting one row of one-dimensional rectangular array on the second plane and on the third plane, respectively;

determining whether an assistant intersection exists between the plane radiation field and two sides of a specific rectangular unit inside the one-dimensional rectangular array in the direction of the third axis, respectively; and if an assistant intersection does not exist, computing the geometric ratio of each rectangular unit inside a first area enclosed by the intersections between the plane radiation field and the row of one-dimensional rectangular array; and repeating the steps to compute the geometric ratio of the rectangular unit with respect to the plane radiation field in each one-dimensional rectangular array.

4. The projection method of 3D ray tracing according to claim 3, wherein the first area has an upper side, a lower side and two sides, a median is provided between the midpoints of the two sides, and the geometric ratio of each rectangular unit covered inside the first area is an integral value of the starting position and the end position of the median passing through each rectangular unit on corresponding positions of the energy intensity relationship line corresponding to the rectangular unit.

5. The projection method of 3D ray tracing according to claim 3, further comprising the following steps:

if n assistant intersections exist between the plane radiation field and the two sides of the specific rectangular unit of the one-dimensional rectangular array, inside a second area enclosed by the intersections between the plane radiation field and the row of one-dimensional rectangular array, constructing a reference line from each assistant intersection respectively to divide the second area into (n+1) sub-areas, wherein n is a positive integer;

computing each sub-geometric ratio that belongs to each rectangular unit inside each sub-area, respectively; and adding sub-geometric ratios obtained from the sub-areas of all rectangular units corresponding to the second area respectively to obtain the geometric ratio of the rectangular unit.

6. The projection method of 3D ray tracing according to claim 5, wherein the sub-area has an upper side, a lower side and two sides, a median is provided between the midpoints of the two sides, an energy intensity relationship line corresponding to the height position of the median is decided, the geometric ratio of each rectangular unit covered inside the sub-area is an integral value of the starting position and the end position of the median passing through each rectangular unit on corresponding positions of the energy intensity relationship line corresponding to the sub-area.

7. The projection method of 3D ray tracing according to claim 2, wherein when the first energy intensity relationship line and the second energy intensity relationship line are horizontal lines, the computing a geometric ratio of each rectangular unit inside an area covered by each row of one-dimensional rectangular array of the plane radiation field further comprise the following steps:

finding intersections between the plane radiation field and the plurality rows of one-dimensional rectangular array on the second plane and the third plane, respectively;

selecting one row of one-dimensional rectangular array on the second plane and on the third plane, respectively;

determining whether an assistant intersection exists between the plane radiation field and two sides of a specific rectangular unit inside the one-dimensional rectangular array in the direction of the third axis, respectively; and if an assistant intersection does not exist, computing the geometric ratio of each rectangular unit inside a first area enclosed by the intersections between the plane radiation field and the row of one-dimensional rectangular array; and repeating the steps to compute the geometric ratio of the rectangular unit with respect to the plane radiation field in each one-dimensional rectangular array.

8. The projection method of 3D ray tracing according to claim 7, wherein the first area has an upper side, a lower side and two sides, a median is provided between the midpoints of the two sides, the geometric ratio of each rectangular unit covered inside the first area is a ratio of the line length of the median passing through each rectangular unit to the length of the median.

9. The projection method of 3D ray tracing according to claim 7, further comprising the following steps:

if n assistant intersections exist between the plane radiation field and the two sides of the specific rectangular unit of the one-dimensional rectangular array, inside a second area enclosed by the intersections between the plane radiation field and the row of one-dimensional rectangular array, constructing a reference line from each assistant intersection respectively to divide the second area into (n+1) sub-areas, wherein n is a positive integer;

computing each sub-geometric ratio that belongs to each rectangular unit inside each sub-area, respectively; and adding sub-geometric ratios obtained from the sub-areas of all rectangular units corresponding to the second area respectively to obtain the geometric ratio of the rectangular unit.

10. The projection method of 3D ray tracing according to claim 9, wherein the sub-area has an upper side, a lower side and two sides, a median is provided between the midpoints of the two sides, and the sub-geometric ratio of each rectangular unit covered inside the sub-area is a ratio of the line length of the median passing through each rectangular unit to the length of the median.

11. The projection method of 3D ray tracing according to claim 1, further comprising a step of multiplying the sub-geometric factor $g_{ij}$ by a ratio factor.

12. The projection method of 3D ray tracing according to claim 1, wherein the emission source further makes a revolving movement.

13. The projection method of 3D ray tracing according to claim 1, wherein the detection module is a detection module in an X-ray imaging system, a computed tomography system, a single-photon emission computed tomography system or a tomosynthesis imaging system.

14. The projection method of 3D ray tracing according to claim 13, further comprising a step of multiplying the sub-geometric factor $g_{ij}$ by a ratio factor.

15. A projection method of 3D ray tracing, comprising the following steps:

providing an emission source disposed between a first detection module and a second detection module, so as to generate a radiation field to be projected to the first detection module and the second detection module, and the first detection module and the second detection module having a plurality of detectors j arranged in an array, respectively, so as to form j×j detector pairs;

defining a 3D space formed by a first axis, a second axis, and a third axis between the emission source and the plurality of detectors arranged in an array, the 3D space having a plurality of voxels i stacked to form a three-dimensional space array, and a sensing plane of the plurality detector pairs corresponding to a first plane defined by the first axis and the second axis, so as to sense the radiation field, each sensed radiation field being obtained by one detector on the first detection module and another detector on the second detection module at the same time;

defining that corners corresponding to each detector pair that senses the radiation field are connected to form a sub-radiation field;

providing a computational processing unit for deduction, so as to obtain a sub-geometric factor $g_{ij}$ of each detector pair corresponding to each voxel i in a corresponding sub-radiation field, the deduction further comprising the following steps:

projecting the sub-radiation field corresponding to each detector pair and the plurality of voxels on a second plane formed by the first axis and the third axis and on a third plane formed by the second axis and the third axis, respectively, so that each detector pair has a corresponding plane radiation field and an adjacent plurality rows of one-dimensional rectangular array arranged into a 2D plane on the second plane and the third plane, respectively, each row of one-dimensional rectangular array having a plurality of rectangular units arranged adjacent to each other, and each voxel corresponding to one rectangular unit on the second plane and corresponding to one rectangular unit on the third plane;

computing a geometric ratio of each rectangular unit inside an area covered by each row of one-dimensional rectangular array of the plane radiation field corresponding to each detector pair on the second plane and the third plane, respectively; and multiplying the geometric ratios of the rectangular units corresponding to each other on the second plane and the third plane to obtain the sub-geometric factor $g_{ij}$ of a voxel corresponding to each detector pair; and combining the sub-geometric factors $g_{ij}$ of all detector pairs with respect to all voxels i to form a geometric factor matrix $G_{ij}$.

16. The projection method of 3D ray tracing according to claim 15, wherein the computing a geometric ratio of each rectangular unit inside an area covered by each row of one-dimensional rectangular array of the plane radiation field further comprises the following steps:

acquiring an energy intensity relationship between the emission source and the detection module at different positions in space; and projecting the energy intensity relationship on the second plane and the third plane to obtain energy intensity relationship lines corresponding to different heights on the second plane and different heights on the third plane, respectively.

17. The projection method of 3D ray tracing according to claim 16, wherein the computing a geometric ratio of each rectangular unit inside an area covered by each row of one-dimensional rectangular array of the plane radiation field further comprises the following steps:

finding intersections between the plane radiation field and the plurality rows of one-dimensional rectangular array on the second plane and the third plane, respectively;

selecting one row of one-dimensional rectangular array on the second plane and on the third plane, respectively;

determining whether an assistant intersection exists between the plane radiation field and two sides of a specific rectangular unit inside the one-dimensional rectangular array in the direction of the third axis, respectively; and if an assistant intersection does not exist, computing the geometric ratio of each rectangular unit inside a first area enclosed by the intersections between the plane radiation field and the row of one-dimensional rectangular array; and repeating the steps to compute the geometric ratio of the rectangular unit with respect to the plane radiation field in each one-dimensional rectangular array.

18. The projection method of 3D ray tracing according to claim 17, further comprising the following steps:

if n assistant intersections exist between the plane radiation field and the two sides of the specific rectangular unit of the one-dimensional rectangular array, inside a second area enclosed by the intersections between the plane radiation field and the row of one-dimensional rectangular array, constructing a reference line from each assistant intersection respectively to divide the second area into (n+1) sub-areas, wherein n is a positive integer;

computing each sub-geometric ratio that belongs to each rectangular unit inside each sub-area, respectively; and adding sub-geometric ratios obtained from the sub-areas of all rectangular units corresponding to the second area respectively to obtain the geometric ratio of the rectangular unit.

19. The projection method of 3D ray tracing according to claim 18, wherein the sub-area has an upper side, a lower side and two sides, a median is provided between the midpoints of the two sides, an energy intensity relationship line corresponding to the height position of the median is decided, the geometric ratio of each rectangular unit covered inside the sub-area is an integral value of the starting position and the end position of the median passing through each rectangular unit on corresponding positions of the energy intensity relationship line corresponding to the sub-area.

20. The projection method of 3D ray tracing according to claim 16, wherein the first area has an upper side, a lower side and two sides, a median is provided between the midpoints of the two sides, and the geometric ratio of each rectangular unit covered inside the first area is an integral value of the starting position and the end position of the median passing through each rectangular unit on corresponding positions of the energy intensity relationship line corresponding to the rectangular unit.

21. The projection method of 3D ray tracing according to claim 16, wherein when the first energy intensity relationship line and the second energy relationship line are horizontal lines, the computing a geometric ratio of each rectangular unit inside an area covered by each row of one-dimensional rectangular array of the plane radiation field further comprise the following steps:

finding intersections between the plane radiation field and the plurality rows of one-dimensional rectangular array on the second plane and the third plane, respectively;

selecting one row of one-dimensional rectangular array on the second plane and on the third plane, respectively;

determining whether an assistant intersection exists between the plane radiation field and two sides of a specific rectangular unit inside the one-dimensional rectangular array in the direction of the third axis, respectively; and if an assistant intersection does not exist, computing the geometric ratio of each rectangular unit inside a first area enclosed by the intersections between the plane radiation field and the row of one-dimensional rectangular array; and repeating the steps to compute the geometric ratio of the rectangular unit with respect to the plane radiation field in each one-dimensional rectangular array.

22. The projection method of 3D ray tracing according to claim 21, wherein the first area has an upper side, a lower side and two sides, a median is provided between the midpoints of the two sides, the geometric ratio of each rectangular unit covered inside the first area is a ratio of the line length of the median passing through each rectangular unit to the length of the median.

23. The projection method of 3D ray tracing according to claim 21, further comprising the following steps:

if n assistant intersections exist between the plane radiation field and the two sides of the specific rectangular unit of the one-dimensional rectangular array, inside a second area enclosed by the intersections between the plane radiation field and the row of one-dimensional rectangular array, constructing a reference line from each assistant intersection respectively to divide the second area into (n+1) sub-areas, wherein n is a positive integer;

computing each sub-geometric ratio that belongs to each rectangular unit inside each sub-area, respectively; and adding sub-geometric ratios obtained from the sub-areas of all rectangular units corresponding to the second area respectively to obtain the geometric ratio of the rectangular unit.

24. The projection method of 3D ray tracing according to claim 23, wherein the sub-area has an upper side, a lower side and two sides, a median is provided between the midpoints of the two sides, the sub-geometric ratio of each rectangular unit covered inside the sub-area is the product of multiplying the ratio of the line length of the median passing through each rectangular unit to the length of the median ratio by the ratio of the height of the sub-area to the height of the rectangular unit.

25. The projection method of 3D ray tracing according to claim 15, wherein the first detection module and the second detection module are detection modules in positron tomography imaging.

* * * * *